(12) United States Patent
Beckmann et al.

(10) Patent No.: US 8,685,337 B2
(45) Date of Patent: Apr. 1, 2014

(54) DEVICE FOR STERILIZING CLOSURES

(75) Inventors: Jörg Beckmann, Stade (DE); Alfred Drenguis, Börnsen (DE)

(73) Assignee: KHS GmbH, Dortmund (DE)

( * ) Notice: Subject to any disclaimer, the term of this patent is extended or adjusted under 35 U.S.C. 154(b) by 405 days.

(21) Appl. No.: 13/059,341

(22) PCT Filed: Aug. 4, 2009

(86) PCT No.: PCT/EP2009/005614
§ 371 (c)(1),
(2), (4) Date: Feb. 16, 2011

(87) PCT Pub. No.: WO2010/031464
PCT Pub. Date: Mar. 25, 2010

(65) Prior Publication Data
US 2011/0142731 A1   Jun. 16, 2011

(30) Foreign Application Priority Data
Sep. 22, 2008 (DE) .......................... 10 2008 048 351

(51) Int. Cl.
*A61L 2/00* (2006.01)
*B08B 3/00* (2006.01)
*A23L 3/00* (2006.01)
*B65G 47/22* (2006.01)

(52) U.S. Cl.
USPC ........... 422/292; 422/286; 422/300; 422/302; 422/304; 134/48; 134/84; 134/105; 134/133; 134/136; 993/360; 993/367; 198/493

(58) Field of Classification Search
USPC ............ 422/286, 292, 300, 302, 304; 134/48, 134/84, 105, 133, 136; 99/360, 367; 198/493
See application file for complete search history.

(56) References Cited

U.S. PATENT DOCUMENTS 4,296,769 A * 10/1981 van der Lugt ................... 134/68

FOREIGN PATENT DOCUMENTS

| DE | 197 27 942 | 1/1999 |
|---|---|---|
| DE | 101 45 102 | 4/2003 |
| DE | 103 59 392 | 5/2005 |
| EP | 0 824 974 | 2/1998 |
| EP | 1 749 747 | 2/2007 |
| FR | 2 789 065 | 8/2000 |
| JP | 11342917 | 12/1999 |
| JP | 2003 128023 | 5/2003 |
| WO | WO 00/27440 | 5/2000 |

* cited by examiner

*Primary Examiner* — Monzer R Chorbaji
(74) *Attorney, Agent, or Firm* — Occhiuti & Rohlicek LLP (57) ABSTRACT

The invention relates to a device for sterilizing caps or the like closures for closing bottles or the like containers. Said device comprises a conveyor system conveying the caps in a direction of conveyance through a treatment section having a plurality of successive treatment stations in the direction of conveyance.

21 Claims, 9 Drawing Sheets

DEVICE FOR STERILIZING CLOSURES

CROSS-REFERENCE TO RELATED APPLICATIONS

This application is the National Stage of International Application No. PCT/EP2009/005614, filed on Aug. 4, 2009, which claims the priority of German Patent Application No. 10 2008 048 351.6, filed on Sep. 22, 2008. The contents of both applications are hereby incorporated by reference in their entirety.

The invention relates to a device according to the preamble of claim 1.

A device of this type is known (DE 101 45 102 A1). In the case of said known device, the closures or caps introduced into a conveying duct are pushed through the conveying duct, connecting tightly to each other in a single-track cap stream or closure stream, by a conveying element formed by a cap wheel. A plurality of treatment stations in the form of nozzle assemblies are provided at the conveying duct, following one after another, spaced apart in the direction of movement of the closures. Disadvantages are, among other things, the relatively low output (number of treated or sterilized closures per unit time) and the danger of the closures becoming jammed in the conveying duct.

In addition, a device for sterilizing closures is known (DE 103 59 392 B3), where by means of a plurality floors, formed in each case by a rotatingly driven disc and by means of inclined planes that connect the floors to one another from top to bottom, the closures are moved through a treatment chamber that is impinged upon with a disinfecting or sterilizing medium. Said known device is structurally expensive, necessitates a relatively large construction and over and above this is very restrictive as regards possible sterilizing methods.

It is the object of the invention to provide a device where a compact design enables closures or caps to be sterilized at optimum quality and at a high output. This object is achieved with a device corresponding to claim 1.

The device according to the invention is flexible with regard to the sterilizing methods used, i.e. it is suitable for the most varied sterilizing methods for sterilizing caps or other closures for closing bottles or similar containers. Nevertheless, the device according to the invention is suitable in a particularly advantageous manner for sterilizing caps or other closures using a sterilizing medium containing hydrogen peroxide ($H_2O_2$) by delivering said sterilizing medium onto the closures in an application phase and by subsequently activating the hydrogen peroxide in an activating phase through the application of energy, for example by means of heating, e.g. by impinging upon the closures with a hot gaseous and/or vaporous activating medium, for example hot sterile air, to release the oxygen radicals from the hydrogen peroxide that effect the sterilization process. The closures are then also dried in the activating phase or a subsequent drying phase.

In the case of a preferred embodiment of the invention, before the sterilizing medium is applied to the closures, the closures are tempered in a pre-treatment phase, in such a manner that said closures then have a pre-heat or pre-treatment temperature. Contrary to the prevailing teaching that assumes that hydrogen peroxide can only be separated as condensate in the application phase on surfaces of closures, and at the same time in particular also in the region of undercuts, in a sufficient amount when said closures have as low a temperature as possible, this special method therefore provides pre-heating the closures before the application phase in a pre-treatment phase or tempering them such that they then have a surface temperature preferably in the range of between 40° C. and 60° C., preferably a surface temperature of 50° C. or ca. 50° C. with deviations of ±2-3° C. It has been shown in a surprising manner that in spite of the tempering of the closures, for example in spite of the pre-heating of the closures to said surface temperature using a hot sterilizing medium containing hydrogen peroxide, which, for example, is applied onto the closures at a temperature in excess of 100° C., a condensate containing hydrogen peroxide is formed in sufficient quantity on the surfaces of the closures and in this case in particular also in any undercuts that may be present.

"Tempering" it his case generally means that the closures are treated such that after the pre-treatment or after the tempering, they have the necessary pre-treatment temperature or surface temperature, for example within the range of between 40° C. and 60° C.

"Tempering" in this case especially means that the closures are heated during the pre-treatment phase to the necessary pre-treatment temperature or surface temperature, for example to the surface temperature within the range of between 40° C. and 60° C. if they have a lower temperature before the pre-treatment, or however if high temperature closures are supplied, for example closures produced directly before sterilization and supplied still at the production temperature, they are cooled to the temperature or surface temperature.

The tempering of the closures in the pre-treatment phase, for example by impinging upon them with a hot sterile gaseous and/or vaporous medium, e.g. with hot sterile air or in another manner, e.g. through radiant energy, in a surprising manner produces a clear shortening of the overall treatment time, including the time of the pre-treatment or the tempering and the application phase, the activating phase and drying phase. It has been shown that without impairing the quality of the sterilization process or of the decontamination, the overall treatment times can be shortened to 15-10 seconds, for example to ca. 12 seconds, with a time of approximately 5 seconds each for the tempering and for the application phase and a time of only 2 seconds or approximately 2 seconds for the activating and drying phase. The surprising element here, in particular, is the extreme shortening of the treatment time for the activating and drying phase although they are not directly connected to the pre-treatment phase.

The individual method steps or treatment phases are controlled such that the surface temperature of the closures does not exceed an upper limit value, for example a limit value in the region of 70° C. or approximately 70° C. Especially in the case of closures that are made entirely or partially of plastics material, this avoids too high a thermal load damaging the closures.

After the activating and drying processes, the closures are then cooled, for example, in the cooling phase down to a temperature that is clearly below 70° C., for example down to a temperature of 30° C. or approximately 30° C. or lower, such that the closures are then available for further use or for processing in a closing machine with good, in particular also constant, reproducible characteristics.

The strongly reduced overall treatment time produces considerable savings on operating costs and in particular, however, also the advantage that the device according to the invention, in which the sterilizing of the closures is carried out in continuous mode, can be realized in a compact manner with a small overall installation size.

Further developments, advantages and application possibilities of the invention are produced from both the following description of exemplary embodiments and from the Figures. In this case all the features described and/or graphically represented are in principle, individually or in arbitrary combination, objects of the invention, irrespective of their summary in the claims or their dependency. The content of the claims is also made a component part of the description.

The invention is explained below by way of the Figures of exemplary embodiments, in which, in detail.

The device given the general reference 1 in FIGS. 1-5 is used for sterilizing closures in the form of caps 2 before said caps are supplied to a closing machine (not shown) for closing bottles or similar containers. The caps 2, for example, are such that are produced at least partially from plastics material and/or are realized as screw-type caps.

A component part of the device 1 is a conveyor or conveying element 3 with a driveable conveyor belt 4, which forms a closed loop, is endlessly circulating and is formed in the manner of a link chain by a plurality of cap baskets 4.1, which are pivotally interconnected and are oriented with their longitudinal extension in each case perpendicular to the conveying direction A. Each cap basket comprises two plate-shaped end pieces 5 spaced apart perpendicular to the conveying direction A and three tubular or rod-like webs 6 and 7 that interconnect the three end pieces 5, of which webs the two webs 6, which are parallel to each other and are spaced apart, form supports for the open or closed side of the cup-like caps 2. The cap baskets 4.1 are pivotally connected to one another at the webs 7 and the end pieces 5. Each cap basket 4.1 forms an accommodating means for a plurality of caps 2, in which accommodating means said caps rest by way of their closed or open side on the webs 6 and are supported laterally by the webs 7, i.e. in the conveying direction A and in opposition to the conveying direction A. Through the described embodiment of the cap baskets 4.1, the caps 2 are accommodated in the cap baskets 4.1 with a small amount of play on all sides and in an exposed a manner as is extensively possible. The individual cap baskets 4.1, in addition, are connected together in relation to the conveyor belt 4 such that the webs 6 are situated on the outside of the loop formed by the conveyor belt 4.

Figure 1:
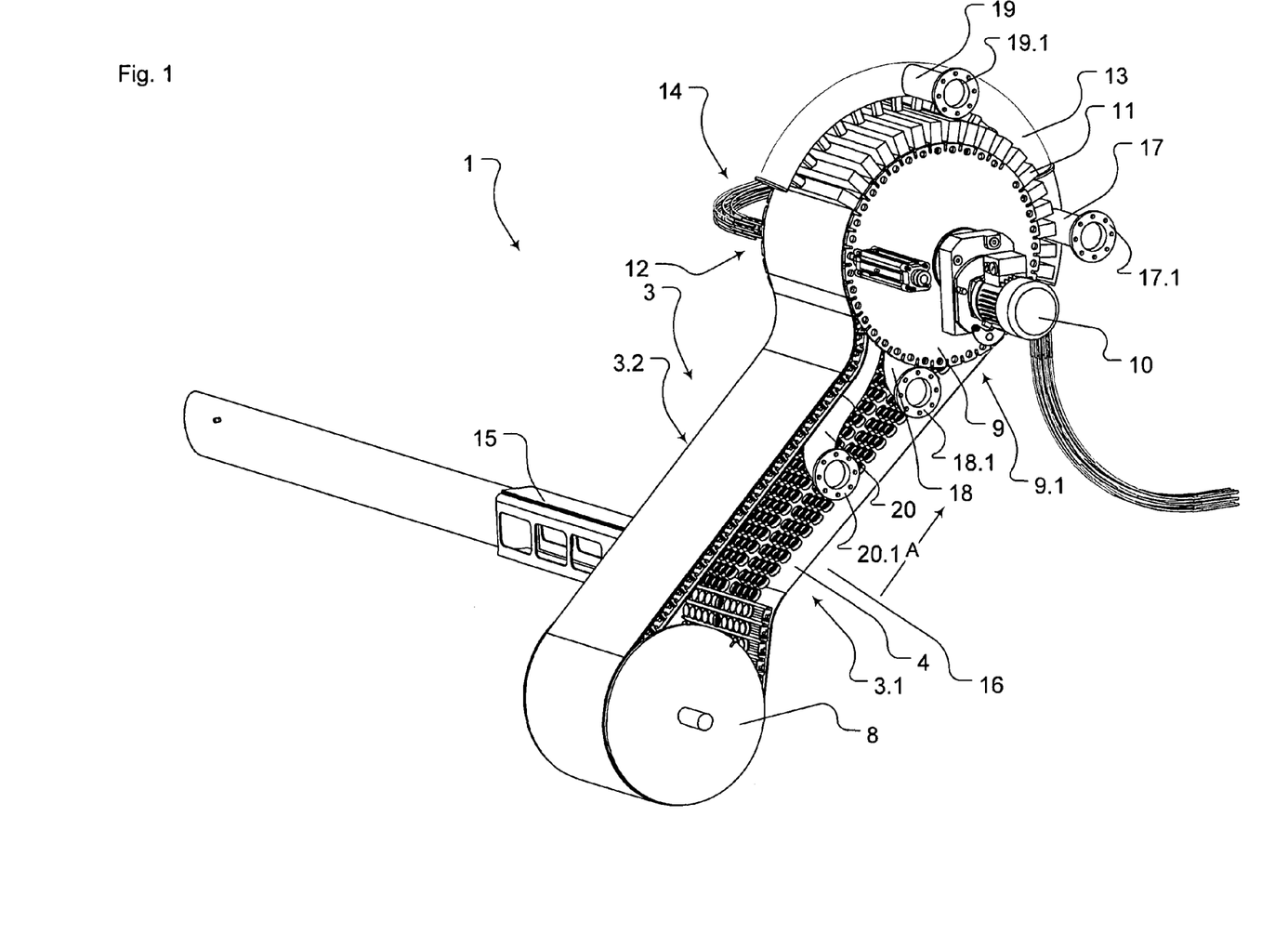
FIG. 1 shows a schematic perspective representation, partially opened, of a device for sterilizing closures for bottles or similar containers.
Figure 2:
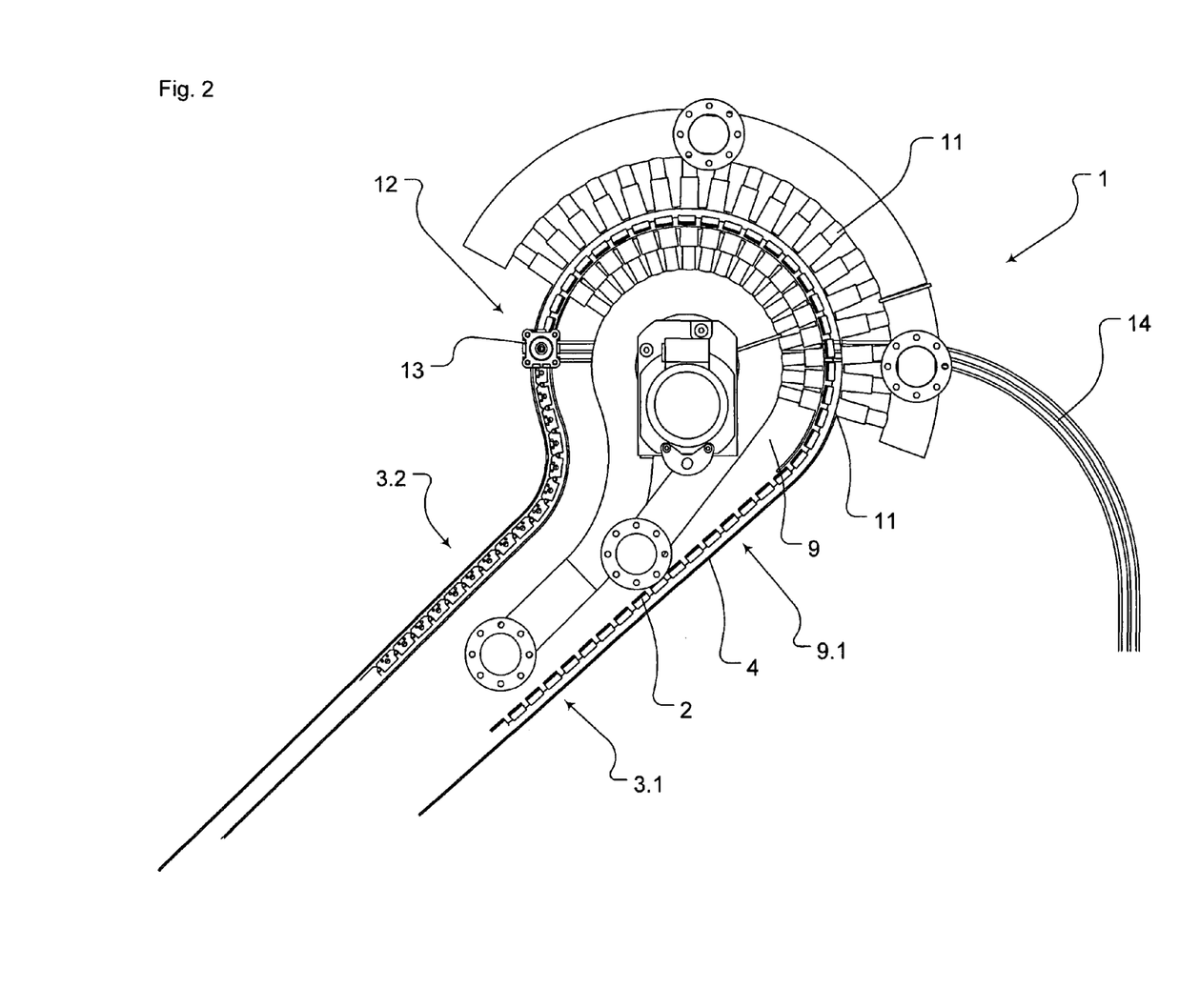
FIG. 2 shows a schematic representation and side view of the sterilizing section of the device in FIG. 1.
Figure 3:
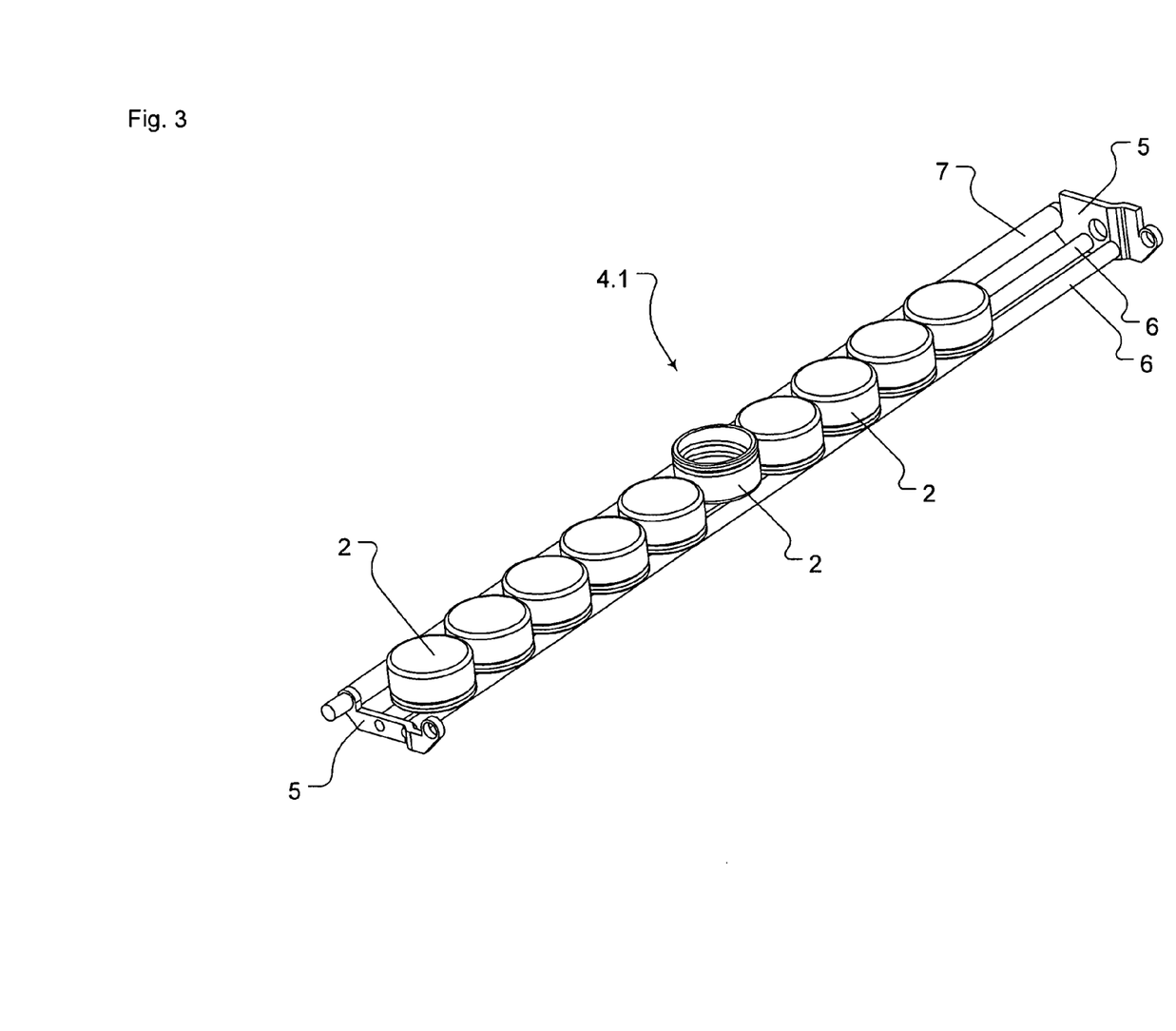
FIG. 3 shows one of the cap baskets of the conveying element of the device in FIGS. 1 and 2.

At the bottom end in FIG. 1, the conveyor belt 4 is guided over a guiding means (not shown) in the region of a drum-like bunker 8 for accommodating the caps 2. At the top end in FIG. 1, the web is guided over a guiding means formed by a sterilizing drum, which is rotatingly driveable by means of an electric motor 10 for moving the conveyor belt 4 in the conveying direction A.

A plurality of treatment stations 11 are provided on the sterilizing drum 9, outside and inside the loop formed that is by the conveyor belt 4, following one after the other in the conveying direction A, in which treatment stations the caps 2 are treated with at least one disinfecting or sterilizing medium, for example in a plurality of treatment steps in the manner described in more detail below.

The conveying element and all further functional elements that interact with the caps, in particular also the bunker 8, the treatment stations 11 and the cap outlet 12, etc. are accommodated by an external housing 15. The method of operation of the device 1 can be described as follows:

The caps 2 are introduced into the bunker 8 by means of a supplying means 15 as an unorganized quantity, from which bunker, with the conveyor belt 4 circulating, a number of caps are then entrained in each case by way of the cap baskets 4.1 that are open to the inside of the bunker 18. Corresponding guiding and/or chicanes ensure that the caps 2 accommodated in each cap basket 4.1 can at best have only two possible orientations, namely resting with the open cap side or the closed cap side on the webs 6 of the cap basket 4.1. Through further measures, for example through corresponding embodiment of an opening, through which the caps 2 pass from the bunker 8 into the cap basket 4.1 and/or through corresponding chicanes, it is ensured that in each case only one part length of each cap basket 4.1 extending perpendicularly to the conveying direction A is occupied by caps 2, for example only 50%-70% of the overall length of each cap basket 4.1. By way of the circulating conveyor belt 4, the caps 2 accommodated in the cap baskets 4.1 are initially moved along the conveying section 3.1 of the conveyor past a sorting station, which is only shown very schematically in FIG. 1 by the reference 16 and in which those caps 2 that do not have the desired correct orientation are ejected, i.e. for example not pointing inwards with their open cap side with reference to the loop formed by the conveyor belt 4, i.e. not resting with their closed cap side or their closed cap bottom on the webs 6. The correctly orientated caps 2 then pass by way of the conveyor belt 4 into the inlet 9.1 of the sterilizing drum 9 and are then moved past the different treatment stations 11 for treatment or sterilization. It is obvious that the treatment stations 11 are realized for this purpose such that in each case they are effective over the entire length of the cap basket 4.1.

Before reaching the treatment stations 11, the caps 2 are spaced apart in each cap basket 4.1 by suitable means, e.g. by rollers, pushers, etc. by using mechanical guides or chicanes and/or through the effect of a gaseous and/or vaporous medium that moves the caps 2, for example the treatment medium used in the respective treatment station 11. In this case in particular, it is possible to move the caps 2 within the respective cap basket 4.1 in the longitudinal direction of the cap basket even during the treatment at the different treatment stations 11 and/or when they are being forwarded from one treatment station 11 to the treatment station following in the conveying direction A, i.e. to displace them and/or rotate them in particular in order to ensure, in this manner, that the caps 2 are treated or sterilized over their entire outside and inside surfaces.

Once they have passed the treatment stations 11, the treated or sterilized caps 2 then reach a cap outlet 12, at which the treated or sterilized caps 2, present in each case in a cap basket 4.1, are ejected as a group by means of an ejecting device 13, for example having an ejecting cylinder, in an axial direction perpendicular to the conveying direction A and parallel to the axis of the sterilizing drum 9, into a cage-like cap duct 14, to be supplied to a closing station of a closing machine associated with the device 1. For this purpose, the ejecting device 13 is driven in a synchronous manner with the pulsed movement of the conveyor belt 4. The empty cap baskets 4.1 pass via the empty section 3.2 back to the bunker 8 to accommodate caps 2 once again. The cage-like cap duct 14, in which the caps 2 are guided on all sides with a small amount of play and are exposed as extensively as possible, is accommodated in a tubular housing (not shown) which is sealingly closed to the surrounding area, said housing is preferably also traversed by a sterilizing medium.

The most varied methods for treating or sterilizing caps 2 are possible using the device 1. In the case of a preferred method, the caps 2 are tempered in the bunker 8 and/or along the conveying section, i.e. are pre-treated such that the caps present in the cap baskets 4.1, when reaching the sterilizing drum 9 or the first treatment station 11 at that location in the conveying direction A, have a pre-treatment temperature or surface temperature of less than 70° C., for example a surface temperature within the range of 30° C. and 60° C., preferably between 35° C. and 40° C., with deviations of ±10° C., preferably with deviations between ±2° C. to 3° C.

If the caps 2 are supplied to the bunker 8 at a temperature that is less than said surface temperature, the tempering is effected by means of pre-heating the caps 2 in the bunker 8 and/or along the conveying section 3.1, for example with a hot, preferably sterile gaseous and/or vaporous medium, e.g. with heated sterile air, or in another manner, e.g. through radiant energy, for example infrared radiation.

If the caps 2 pass into the bunker 8 and out of said bunker into the cap baskets 4.1 with a surface temperature that is clearly above the aforementioned temperature, for example because the caps 2 were supplied to the bunker 8 immediately after their production and consequently still have the production temperature resulting from the production process, the tempering in the bunker 8 and/or along the conveying section 3.1 can also comprise cooling the caps 2 down from the higher production temperature to the pre-treatment temperature.

At the individual treatment stations 11, according to said preferred method, the treatment of the caps 2 is effected initially in an application phase at one or at a plurality of treatment stations 11 following one after another in the conveying direction A, by applying a hot sterilizing medium containing hydrogen peroxide (H2O2), which comprises a mixture of a heated gaseous and/or vaporous medium, for example heated sterile air and hydrogen peroxide (H2O2) in vaporized form. Following this, in an activating phase at one or at a plurality of treatment stations 11 following one after another in the conveying direction A, the sterilizing medium applied to the caps 2 is activated by means of impingement with a heated vaporous and/or gaseous activating medium, for example by means of impingement with heated sterile air, such that by activating the hydrogen peroxide contained in the sterilizing medium, i.e. by splitting free oxygen radicals from the hydrogen peroxide, the caps 2 are sterilized at the high quality required. After activating the sterilizing medium, in the at least one treatment station 11 or in an additional treatment station used for this purpose, the caps 2 are dried by way of the heated activating medium or by way of heated sterile air.

It has been shown in a completely surprising manner that by tempering the caps 2 before supplying them to the at least one treatment station 11 for applying or delivering the sterilizing medium, a clear shortening of the overall treatment length can be achieved, and this includes the time of the pre-treatment or the tempering, the application phase and the activating phase as well as the drying phase. It has also been shown in a surprising manner that in spite of tempering the caps 2, condensate, necessary for the sterilizing process, formed from the sterilizing medium used in the application phase is achieved on all surface regions of the caps 2, in particular even in surface regions that are difficult to access, like undercuts etc. It has also been shown that without impairing the quality of the sterilizing process or of the rate of decontamination, the entire treatment time can be shortened to 15-10 seconds, for example to ca. 12 seconds, with a time of approximately 5 seconds for the application phase and a time of only 2 seconds or approximately 2 seconds for the activating and drying phase.

In a preferred manner after the drying and before discharging the caps 2 into the cap duct 14, the caps 2 are cooled again down to a surface temperature that is clearly less than 70° C., for example to a surface temperature below 50° C., e.g. to a surface temperature of approximately 30° C., in order also for caps 2 produced from plastics material, to obtain the strength necessary in particular for the closing process before the caps 2 are supplied to the closing machine or its closing tools. The cooling of the caps 2 can also be effected in the cap duct 14, for example by means of a cooling sterile gaseous and/or vaporous medium, e.g. with cool sterile air, which traverses the tubular housing that accommodates the cap duct 14.

In addition to reducing the overall treatment time, this method, in surprising manner, also produces a reduction in operating costs and a reduction in the installation size of the device 1. In the case of filling or closing systems with a conventional output, just the operating costs saved can be in the order of several hundred thousand Euros. In spite of the shortened treatment time, it is also possible to achieve the drying of the caps 2 at the same time in the at least one treatment station that is used for activating the sterilizing medium.

In addition, in spite of the shortened treatment time, the residual amount of hydrogen peroxide in the treatment medium discharged from the relevant treatment station during the activating phase is clearly below a legally prescribed value. In each case, however, the method steps or treatment phases are controlled such that in said treatment phases a defined temperature profile is maintained in order, on the one hand, to meet the demands with regard to an optimum sterilizing effect and as small as possible an amount of residual hydrogen peroxide, and on the other hand, to ensure that the surface temperature of the caps 2 does not exceed an upper limit value, for example a surface temperature of 70° C., in order, in this manner, to prevent any thermal damage to the caps 2, in particular those made of plastics material, and also to prevent any impairment to the strength and mechanical stability of the caps 2.

Distributor tubes 17-20 with corresponding connections 17.1-20.1 for connection to external supply lines are provided for supplying the treatment media to the individual treatment stations 11. The distributor tubes 17 and 18, here, are used to supply the sterilizing medium containing hydrogen peroxide—the distributor duct 17 supplies it to the treatment stations 11 located on the outside with reference to the loop of the conveyor belt 4 and the distributor duct 18 supplies it to the treatment stations 11 located on the inside with reference to the loop of the conveyor belt 4. The distributor tubes 19 and 20 are used to supply the sterile vaporous or gaseous medium, for example for supplying sterile air—the distributor duct 19 supplies it to the treatment stations 11 located on the outside and the distributor duct 20 supplies it to the treatment stations 11 located on the inside. In addition, at least one exhaust air duct is provided in the region of the sterilizing drum 9.

FIG. 4 once again shows a simplified representation of the individual treatment stations 11 following one after another in the conveying direction A, just one group of treatment stations 11, namely for example the treatment stations 11 located on the outside or the treatment stations 11 located on the inside being represented in this Figure.

Figure 4:
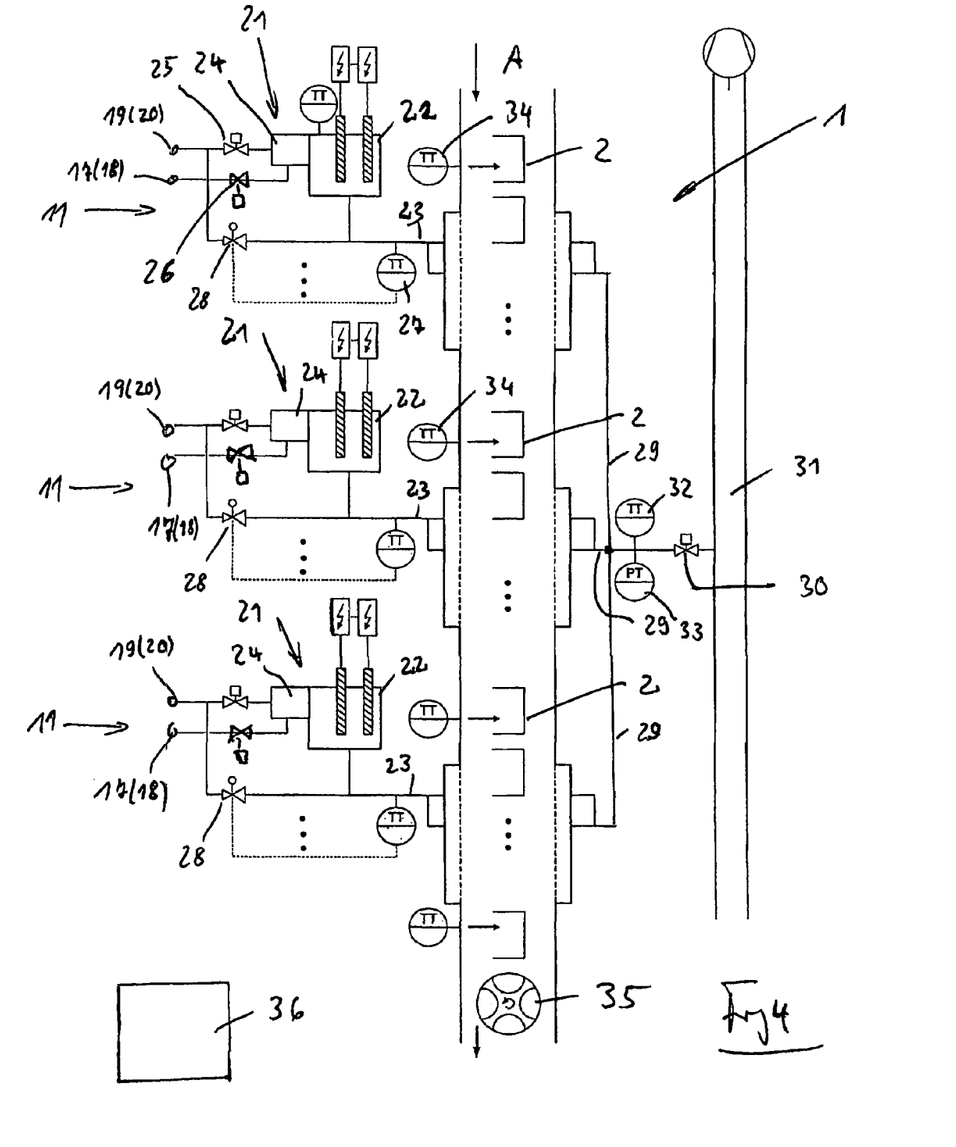
FIGS. 4 and 5 each show a very schematic representation of the sterilizing section of the device in FIGS. 1-3 with different embodiments, together with a plurality of treatment zones provided at said treatment section.

Each treatment station 11, in the case of the embodiment represented, comprises, in a very compact design, a device 21 for the optional preparation of heated sterile air for activating the sterilizing medium and also for preparing the hot sterilizing medium in the form of a mixture of heated air and hydrogen peroxide (H2O2). For this purpose, the device 21 of each treatment station 11 is realized with, among other things, a heater 22, which is connected on the outlet side via a line 21 to outlet nozzles or openings in the relevant treatment station 11. On the input side, the heater 22 has associated therewith a mixing head 24 or the heater is connected downstream of the mixing head 24, which in its turn is connected via a control valve 25 to the distributor duct 19 or 20 for supplying the sterile air. At the same time, the mixing head 24 is connected via a control valve 26 to the distributor duct 17 or 18 containing the hydrogen peroxide, such that through corresponding actuation of the control valves 25 and 26 in the mixing head 24, by means of spraying finely distributed hydrogen peroxide into the sterile air stream, an aerosol can be created from sterile air and hydrogen peroxide, which (aerosol) is then heated in the heater 22 to form the hot sterilizing medium.

The line 23 is connected to the distributor duct 19 or 20 via a control valve 28 that is controlled by a temperature sensor 27 in the line 23. The treatment stations 11, in addition, are connected via an exhaust air line 29 with control valve 30 to an exhaust air duct 31. A temperature sensor 32 and also a sensor 33, which is realized, for example, as a pressure or flow meter and/or as a sensor for detecting the H2O2 proportion in the exhaust air discharged via the exhaust air line 29, are provided, among other things, in the exhaust air line 29, which is common to all treatment stations 11. In addition, each treatment station 11 has associated therewith, for example, an additional sensor 34 that detects the temperature of the treatment zone formed by the treatment station 11 and/or of the treated caps 2. A sensor device 35, e.g. in the form of a cap wheel, is provided, for example, at the outlet of the treatment section formed by the treatment stations 11; said sensor device interacts with control logic 36 and determines the number of caps 2 actually passing the treatment stations 11 or the treatment section and consequently the actual output of the device 1.

A characteristic of the treatment section formed by the treatment stations 11 or of the device 1 is that each treatment station 11 can be operated as an application station for applying the hot sterilizing medium containing the hydrogen peroxide, by the corresponding device 21 preparing hot sterilizing medium at the line 23, for which, via the open control valve 26, hydrogen peroxide in the mixing head 24 is sprayed into the sterile air stream supplied via the open control valve 25, such that said mixture or aerosol, after being heated in the heater 22, is available as hot sterilizing medium at the line 23 and can be applied to the caps 2 moved past the relevant treatment station 11 in a pulsed manner.

Through corresponding actuation, in particular of the control valves 25, 26 and 28, each treatment station 11 can also be operated as an activating station for activating the sterilizing medium applied to the caps 2, by the corresponding device 21 making available heated sterile air for the activation process at its line 23, for which the sterile air supplied via the open control valve 25 is heated in the heater 22 and is mixed with non heated sterile air via the control valve 28 to control the temperature.

In addition, it is also possible to utilize at least one treatment station 11 for the tempering process or for an additional tempering of the caps 2, once again by making available heated sterile air at the line 23 or at the nozzle openings connected to said line, by heating the air in the heater 22 and controlling the temperature by mixing-in non heated sterile air via the control valve 28.

In particular, the control of the individual treatment stations 11 or of their devices 21 is preferably effected as a function of the output of the device 1 and/or as a function of the conveying speed at which the caps 2 or the cap baskets 4.1 are moved through the treatment stations 11 and consequently through their treatment zones, i.e. as a function of the conveying speed of the conveyor belt 4, controlled by the control device 36 in such a manner that the number of treatment stations 11 operated in each case as application station and as activating station is adapted to the output of the device and/or to the conveying speed. Where the output or conveying speed of the conveyor 4 is very low, for example only one treatment station 11 is used in each case for the application of the sterilizing medium and for the activating of the sterilizing medium, whilst the remaining treatment stations 11 are deactivated. Where the outputs are greater, correspondingly more treatment stations 11 following one after the other in the conveying direction A are used in each case for the application of the sterilizing medium and for the activation of the sterilizing medium, such that in spite of the increased conveying speed of the conveyor belt 4 and consequently in spite of the increased speed at which the caps 2 are moved through the treatment section formed by the treatment stations 11, the required effect of the sterilization is obtained. If tempering is also effected in the region of the sterilizing drum 9, for example the pre-heating of the caps 2, it is then also possible to control or regulate the number of treatment stations 11 used for said tempering as a function of the conveying speed of the conveyor belt 4 and/or as a function of the actual output of the device 1, i.e. to utilize only one treatment station 11 for the tempering process where the output and conveying speed are modest and where the output and conveying speed are greater to utilize a correspondingly higher number of treatment stations 11 for the tempering process. By switching treatment stations 11 on or off, which is preferably effected in each case starting from the inlet 9.1 of the sterilizing drum in or in opposition to the conveying direction A, it is possible, in particular, to adapt rapidly to any changes in the output of the device 1.

Figure 5:
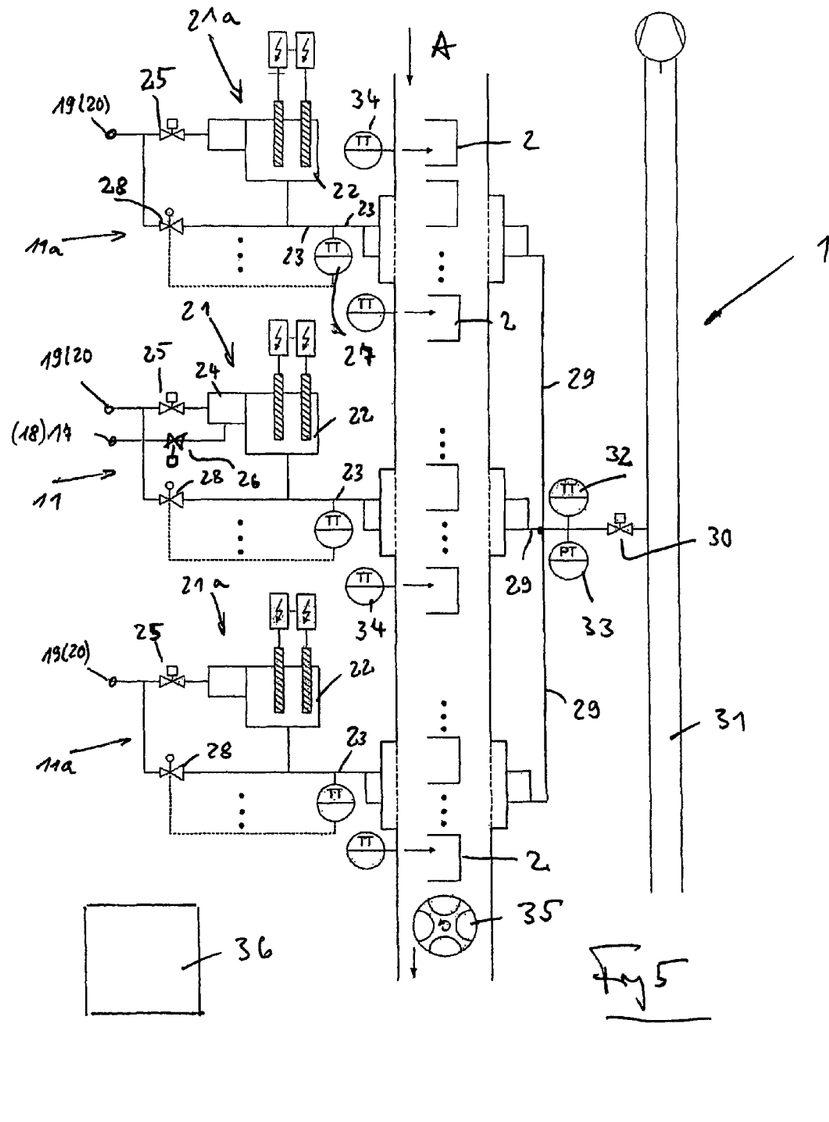

FIG. 5 shows, as another embodiment, a treatment section formed by the plurality of treatment stations 11, said treatment section differing from the treatment section in FIG. 4 essentially in that a plurality of groups, for example three groups of treatment heads 11a and 11 are provided following one after another in the conveying direction—following the inlet 9.1 in the conveying direction a group of treatment stations 11a, connecting thereto a group of treatment stations 11 and connecting thereto once again a group of treatment stations 11a. To simplify the representation, only one treatment station 11 or 11a is shown for each group in FIG. 3.

The treatment stations 11 have once again associated therewith in each case a device 21 and the treatment stations 11a in each case a device 21a, which differs essentially from the device 21 in that the means for mixing or introducing hydrogen peroxide into the sterile air stream (e.g. mixing head 24, valve 26 and the connection to the distributor duct 17 or 18) are omitted, it being possible to operate the treatment heads 11a therefore in each case exclusively as pre-treatment head for the tempering process or as activating head for activating the sterilizing medium.

The control of the individual treatment heads 11 and 11a or of their devices 21 and 21a is then effected, for example, in general such that the caps 2, once again after reaching the sterilizing drum 9, are tempered or pre-heated for example additionally in one or in a plurality of method steps, for which at least one treatment station 11a of the first group is operated as a pre-heat or pre-treatment station, such that in a further method step the caps 2 are impinged upon with the hot sterilizing medium, comprising the hot sterile air and the hydrogen peroxide, for which at least one treatment station 11 of the second group is operated as application station and that in a further method step the sterilizing medium is activated, for which at least one treatment station of the third group is operated as activating station.

In the case of this embodiment also, the activated treatment stations 11 and 11a are opened and closed in a controlled manner within the respective group as a function of the output of the device 1 and/or as a function of the conveying speed of the conveyor belt 4. If tempering or subsequent tempering of the caps 2 is not necessary at the sterilizing drum 9, deviating from the representation in FIG. 5 only two groups of treatment stations are necessary, namely the treatment stations 11 as first group and the treatment stations 11a as the second group following in the conveying direction A.

As mentioned above, FIGS. 4 and 5 show a simplified representation in each case of only the treatment stations 11 and 11a that are provided in the region of the sterilizing drum 9 on one side of the conveyor element 4, for example on the outer side with reference to the loop of the conveyor belt 4. The treatment stations 11 or 11a are then realized in an identical manner on the inside.

It has been assumed above that each treatment station 11 and 11a, among other things, has an its own heater 22 and each treatment station 11 also has its own mixing head 24 and, in addition, the control valves 25, 26 and 28 as well as temperature sensors 27 are provided for each treatment station. Obviously it is also possible, to simplify the treatment stations 11 and 11a, to provide the aforementioned elements, in so far as is necessary, common to all the treatment stations, for example also in the manner that the aforementioned functional elements or devices 10 or 10a are provided common to outside and inside treatment stations 11 and 11a that are associated with one another or to a group of such treatment stations together.

Figure 6:
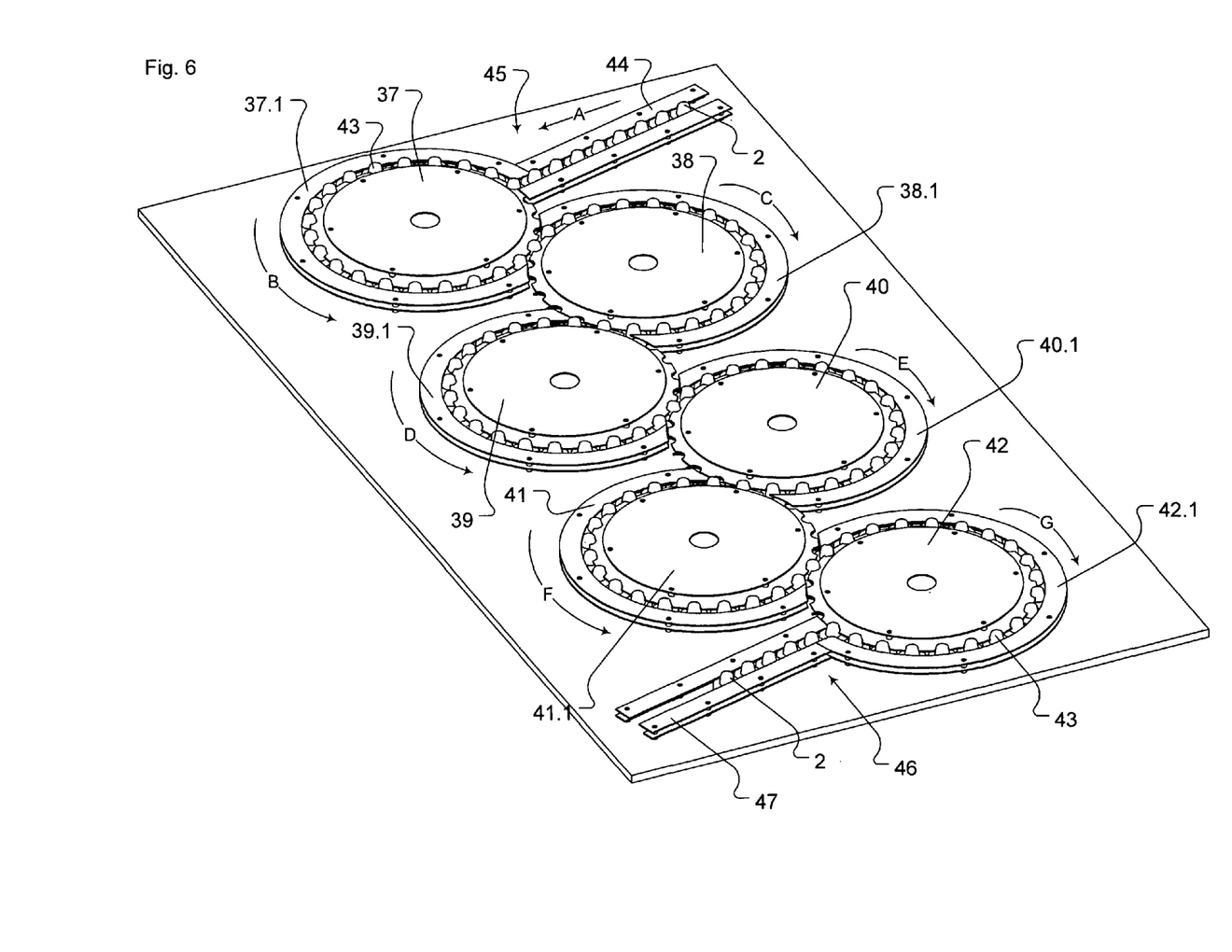
FIG. 6 shows a very schematic representation of another embodiment of the device according to the invention.

FIG. 6 shows a very schematic representation of a device 1a or of its conveyor 3a, which is formed by a plurality of conveying wheels 37-42 that are directly connected to one another in the conveying direction A with associated outer guides 37.1-42.1. The conveying wheels 37-42 are each realized on their circumference with a plurality of accommodating means 43 for accommodating at least one cap 2 and are driven in a synchronous manner in opposite directions (arrows B-G) about parallel axes, in such a manner that each cap 2, supplied via a supplying means 44 to a cap inlet 45 of the device 1a, by being transferred from one conveying wheel 37-41 to each connecting transport wheel 37-41 in the conveying direction A, reaches the cap outlet 46, said outlet connecting to a cap duct 47 that leads to the closing station of a closing machine.

The caps 2 accommodated in the accommodating means 43 are consequently moved along arcuate part sections of the treatment or conveying section of the conveyor 3a by means of the conveying wheels 37-41 that are rotatingly driven in opposite directions, said part sections being formed by said conveying wheels and connecting to each other, being moved past treatment stations (not shown) corresponding to treatment stations 11 or 11a where the caps 2 are sterilized, for example by means of preliminary tempering or pre-heating, by subsequently impinging upon the caps 2 with the sterilizing medium containing hydrogen peroxide and by subsequently activating the sterilizing medium by impinging upon the caps with the hot vaporous and/or gaseous activating medium, for example by impinging upon them with hot sterile air.

The individual method steps are preferably each carried out at separate conveying wheels 37-42, i.e. the treatment stations necessary for the individual method steps are each provided at independent conveying wheels 37-42. The advantage of the device 1a compared to the device 1 is, among other things, that the conveying wheels 37-42 and their accommodating means 43 can be sterilized together with the caps 2 in a substantially simpler and quicker manner than is possible in the case of the link-chain-like conveyor 4 of the conveying element 3. In addition, the conveyor 3a can be realized in a cost-efficient and very compact manner, i.e. with a smaller overall installed size. The individual conveying wheels 37-42 and the associated guides 37.1-42.1 can easily be changed in the case of format modifications, i.e. to process caps 2 or other differently sized closures.

The conveying wheels 37-42 are realized, for example, such that there is only space for one cap 2 in each accommodating means 43. In principle, however, it is also possible to realize the conveying wheels 37-42 as drums in such a manner that in each accommodating means 43 in the direction of the axis of the respective conveying wheel there is space for at least two or even more than two caps 2.

Figure 7:
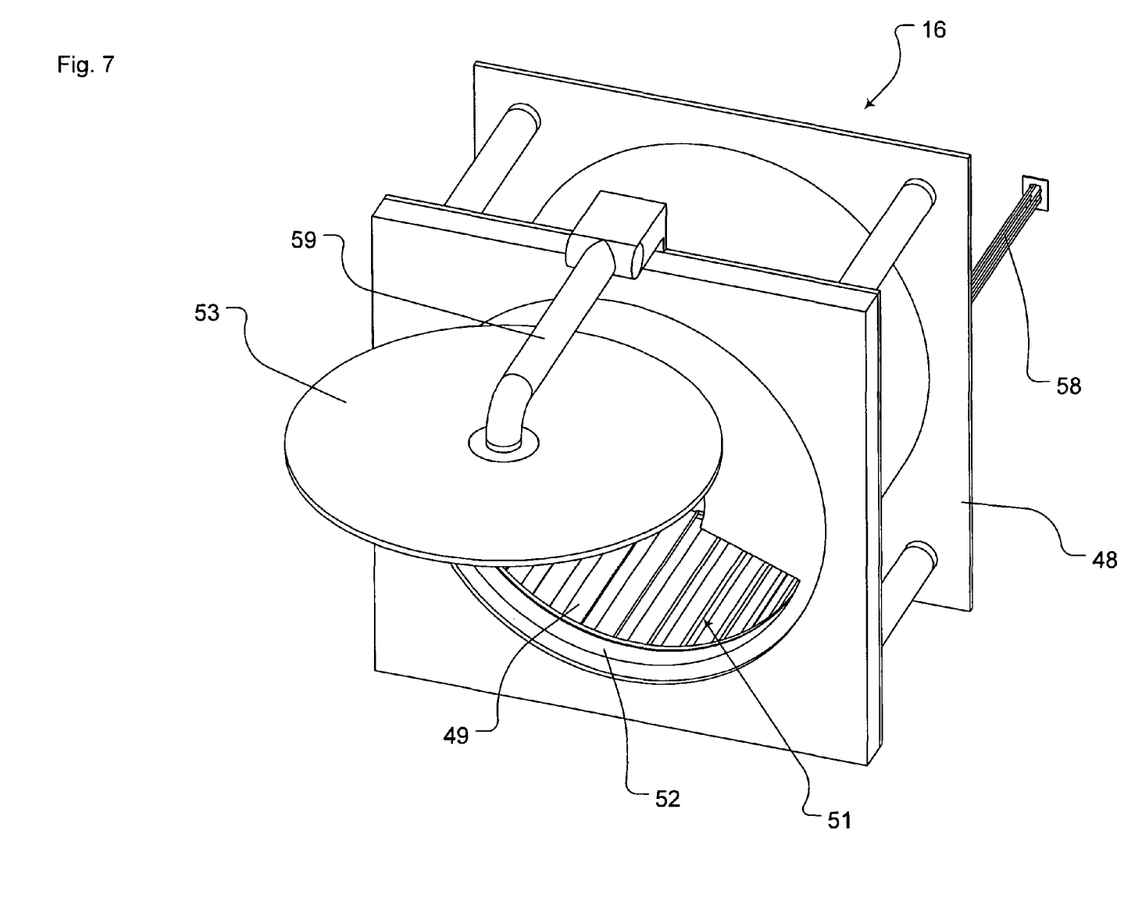
FIGS. 7 and 8 show a perspective representation of a drum for sterilizing closures for bottles or similar containers.
Figure 8:
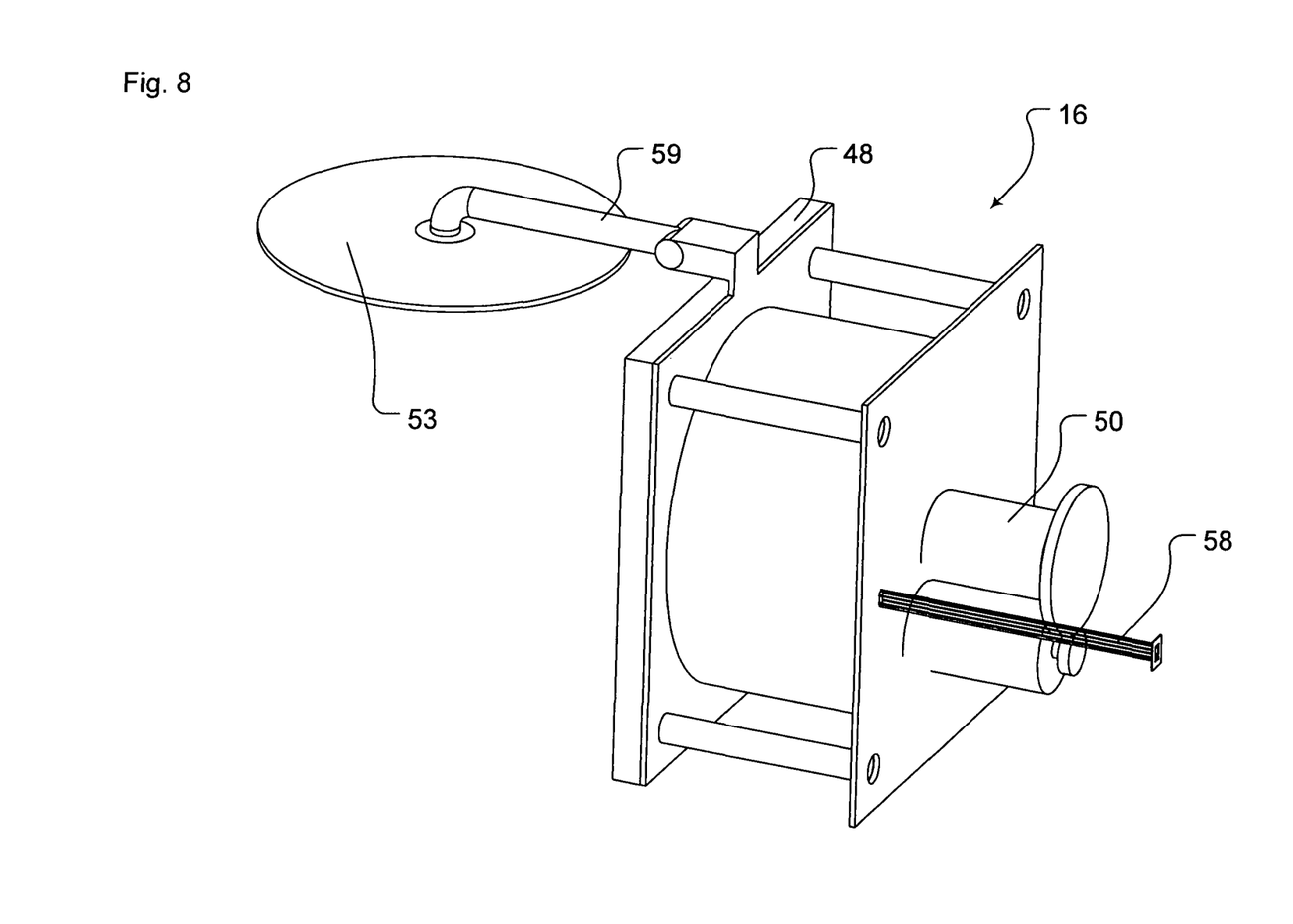
Figure 9:
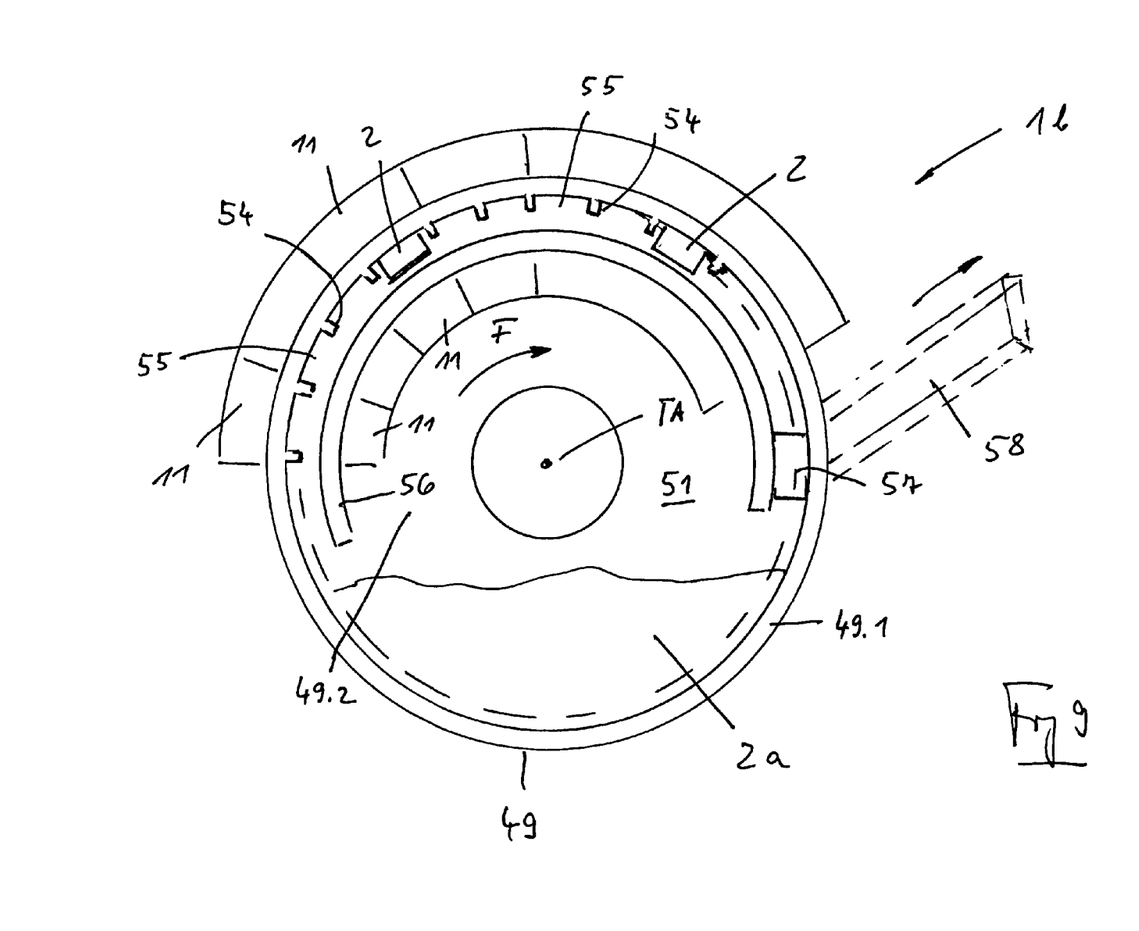
FIG. 9 shows a schematic representation of the drum in FIGS. 7 and 8.

FIGS. 7-9 show, as a further embodiment, a device 1b for sterilizing and/or disinfecting caps 2. The device 1b essentially comprises a housing 48, in which is provided a drum 49, which can be rotatingly driven about its horizontal drum axis TA by means of a drive 50 (arrow F), preferably in a pulsed manner. The drum 49 is realized such that it essentially comprises a circular cylindrical drum wall 49.1 that surrounds the drum axis TA in a concentric manner and a drum bottom 49.2 at which the drum 49 is rotatably mounted by means of a shaft (not shown) in a bearing of the housing 48. At the front of the device 1b or of the housing 48, the interior 51 of the drum 49 is accessible via an opening 52, which is circular in the embodiment represented, is provided in the front wall of the housing 48 and is closable by means of a circular-disc-shaped flap 53. The flap 53 is produced, for example, from a transparent material, for example acrylic glass, such that the method of operation of the device 1b is able to be optically monitored.

On the inside surface, the circular cylindrical drum wall 49.1 is provided with a plurality of projections or webs 54, which each extend parallel to the drum axis TA over the entire axial width of the drum wall 49.1, such that in each case between two webs 54 following one after the other in the circumferential direction of the drum 49 an accommodating means is formed 55 for accommodating a plurality of caps 2, which are located in each accommodating means in a row parallel to the drum axis TA.

The reference 56 refers in FIG. 9 to an inner guiding means, which extends in an arcuate form over the angular region of the rotational movement of the drum 49, but is held in a suitable manner on the housing 48 so as not to be entrained with said drum. The guiding means 56 is located and realized such that the caps 2 accommodated in the accommodating means 55 are supported at least at the angular region of the rotational movement of the drum 49 by the guiding means 56, at which angular region the caps 2 would fall out of the accommodating means 55 for reasons of gravity if the guiding means 56 were not provided there. The guiding means 56 extends as far as a cap outlet 57, past which the individual accommodating means 55 are moved with the drum 49 and at which the caps 2 located in the respective accommodating means 55 are discharged as a cap group, in which the caps 2 are arranged side by side in rows, into a cap duct 58 to be forwarded, for example, to the cap accommodating means of a closing machine.

The caps 2 to be treated or to be sterilized and/or to be disinfected are supplied to the drum interior 51 via a cap supplying means. In the embodiment represented, said supplying means is formed by a tube section 59, which at the same time is also the support for the pivotal flap 53. The caps 2 to be treated pass via the tube section 59 in the region of the drum axis TA into the drum interior 51 within the guiding means 56 and then in the bottom region of the drum interior 51 form a cap store, which is given the reference 2a in FIG. 9 and contains the caps 2 in an unorganized quantity.

Through the rotational movement of the drum 49, the caps 2 in the cap store 2a are distributed over the entire axial width of the drum 49 and are entrained in a sorted manner with the accommodating means 55 such that the caps 2 have a predetermined orientation in said accommodating means 55, for example with the open cap side, with reference to the drum axis TA, oriented radially inward. Said sorting is achievable, for example by realizing the webs 54 in a corresponding manner.

A plurality of treatment heads or treatment stations 11 are provided along the conveying section, along which the caps, located in the accommodating means 55, are moved as far as the cap outlet 58 and along which the guiding means 56 also extend, said treatment heads or stations extending in each case over the entire axial width of the drum 49 and by way of which the caps 2 are at least sterilized and/or disinfected. The treatment stations 11, in this case, are located and/or realized such that the caps 2 are treated over their entire inside and outside surfaces, for example at least by applying the hot sterilizing medium containing hydrogen peroxide in an application phase and by subsequently activating said sterilizing medium with the hot activating medium.

In this embodiment also it is once again possible to control the rotating or conveying speed of the drum 49 and consequently the speed at which the caps 2 are moved through the treatment zones 11 as a function of the requirement for treated caps 2, i.e. as a function of the output of the closing machine, the number of treatment heads or treatment stations 11 activated in each case also being controlled as a function of the conveying speed of the output, such that the necessary treatment times are maintained in an optimum manner.

The discharging of the treated caps 2 at the cap outlet 57 into the cap duct 58 is effected, for example, by means of a mechanical ejector or slider, which is activated in a synchronous manner with the rotational movement of the drum 49 and/or by means of blowing with a sterile gaseous and/or vaporous medium, for example sterile blowing air.

The particular advantage of the device 1b is in a simplified structural embodiment and in particular also in that both the sorting of the caps 2 and the movement of the caps 2 through the treatment section formed by the treatment stations 11 is effected by way of the drum 49. In addition, the device 1 is suitable for continuous treatment of the caps 2 in that the caps 2 to be treated are supplied in a controlled manner to the drum interior 51 via the tube section 59 and are removed from the cap store 2a continuously by the rotating drum 49. In this case it is only necessary to open the flap 53 in the event of a fault.

The device 1b, however, is also suitable for the batchwise treatment of the caps 2, for example in the manner that in each case a number of caps 2 is introduced into the drum interior 51 via the open flap 43, the caps 2 are then sorted in the aforedescribed manner and treated in the accommodating means 55 at the treatment stations 11 and the sterilized and/or disinfected caps 2 are then supplied to the cap duct 58 via the cap outlet 57.

A particular advantage of the device 1b, in addition, is that the drum 59 is realized, in particular at its drum inside surface that comes into contact with the caps 2, at least extensively smoothly and without any undercuts, intermediate spaces, gaps, etc. that are difficult to access and the drum 49 and its accommodating means 55 are not only continuously sterilized and/or disinfected when moving past the treatment stations 11 but they also move outside the treatment section formed by the treatment stations 11 in a sterile space or an extensively sterile space, such that with a simplified structural embodiment and a high level of operating reliability of the device 1b, a high level of quality of sterilization or a high level of decontamination are also achievable by using this device.

The invention has been described above by way of exemplary embodiments. It is obvious that numerous modifications and conversions are possible without in any way departing from the inventive concept underlying the invention. Thus, the devices 1 and 1a are suitable for sterilizing not only caps 2 in the current sense, but also for sterilizing other types of closures that are used to close bottles or similar containers. In addition, it is possible to provide all the treatment stations on one common conveying wheel or on one common conveying drum.

Common to all the described embodiments of the invention, however, is that the respective conveying element or the respective conveyor forms baskets or accommodating means in which the caps 2 are accommodated in a defined and/or positive locking manner when being conveyed between a closure inlet, for example the bunker 8 or the cap inlet 45 or the cap store 2a, and a closure outlet, for example the cap outlet 12 or 46 or 57 on the conveying element or conveyor at least in the conveying direction A or F, such that an optimally controlled treatment of the caps 2, in particular as a function of the output of the device 1 or 1a or of the conveying speed, is possible by maintaining the treatment times necessary for optimum sterilization at the individual treatment stations, and also a simplified introduction of the caps 2 at the cap outlet 12 or 46 or 57 into a cap duct 14 or 47 or 58 that connects at that location and leads to the closing station of a closing machine.

LIST OF REFERENCES 1, 1a Device
2 Closure or cap
2a Cap store
3 Conveyor or conveying element
3.1 Conveying section
3.2 Empty section
4 Conveyor belt
4.1 Cap basket
5 End section
6, 7 Web
8 Bunker
9 Sterilizing drum
9.1 Inlet of the sterilizing drum or of the treatment section
10 Drive motor
11, 11a Treatment station
12 Cap outlet
13 Ejector device
14 Cap duct
15 Cap supplying means at bunker 8
16 Sorting station
17-20 Distributor tube
17.1-20.1 Connection 21 Device
22 Heater
23 Line
24 Mixing head
25, 26 Control valve
27 Temperature sensor
28 Control valve
29 Line
30 Valve
31 Exhaust air duct
32, 33, 34 Sensor
35 Sensor element
36 Control device
37-42 Conveying wheel or conveying drum
37.1-42.1 Guiding means
43 Accommodating means
44 Supplying means
45 Cap inlet
46 Cap outlet
47 Cap duct
48 Housing
49 Drum
49.1 Drum circumferential wall
49.2 Drum bottom
50 Driving means
51 Drum interior
52 Opening at the front of the housing 48
53 Flap for closing the opening 52
54 Web
55 Accommodating means
56 Guiding means
57 Cap outlet
58 Cap duct
59 Tube section
A Conveying direction
B-G Direction of rotation of the conveying wheels 37-42
F Direction of rotation of the drum 59
TA Drum axis

The invention claimed is:

1. An apparatus for sterilizing closures for closing containers, said apparatus comprising: a sterilizing region for sterilizing closures, said sterilizing region including at least one of a treatment section and a treatment chamber, a bunker for storing closures prior to sterilization thereof, an ejector device for ejecting closures following sterilization thereof, closure-accommodating baskets, each of which accommodates closures, a circulating conveying element for moving said closure-accommodating baskets along a conveying direction in a closed loop from said bunker, where they are loaded with closures, through said sterilizing region, where said closures are sterilized, to said ejector device, where said basket is emptied of said closures, and back to said bunker, wherein the closures accommodated in the closure-accommodating basket, at least in the conveying direction have a defined position and/or orientation with reference to the circulating conveying element.

2. The apparatus of claim 1, wherein the circulating conveying element is configured for obtaining the closures from an unorganized quantity of closures and for sorting the closures into the defined position and/or orientation.

3. The apparatus of claim 1, wherein the closure-accommodating baskets are configured for accommodating closures that are connected to each other along a direction perpendicular to the conveying direction or closures that are offset one against another.

4. The apparatus of claim 1, wherein the circulating conveying element comprises: a drivable conveyor belt that forms an endlessly circulating closed loop, and wherein the closure-accommodating baskets are provided on the conveyor belt following each other in the conveying direction.

5. The apparatus of claim 4, wherein the conveyor belt comprises a link chain, and wherein the closure-accommodating baskets are pivotally-interconnected and attached to one another in the conveying direction.

6. The apparatus of claim 5, wherein each of the baskets comprises a cage for exposing the accommodated closures.

7. The apparatus of claim 4, wherein the conveyor belt is guided through the bunker.

8. The apparatus of claim 7, wherein the bunker comprises a heating device for pre-heating the closures.

9. The apparatus of claim 4, further comprising treatment stations following one after the other in the conveying direction on at least one side of a loop formed by the conveyor belt.

10. The apparatus of claim 1, further comprising: means for guiding the closures, said means for guiding the closures being provided on the path of movement of the closure-accommodating baskets and configured for removing incorrectly oriented closures from the closure-accommodating baskets before such incorrectly oriented closures reach the sterilizing region.

11. The apparatus of claim 1, further comprising, at the sterilizing region, means for moving the closures in the basket in a direction perpendicular to the conveying direction and/or means for spacing the closures apart.

12. The apparatus of claim 1, wherein the ejector device is disposed at a closure outlet for the simultaneous discharging of the closures from the closure-accommodation basket.

13. The apparatus of claim 1, wherein the circulating conveying element comprises conveying elements directly connected to each, wherein said conveying elements are selected from the group consisting of conveying wheels and conveying drums, wherein the conveying elements are provided on circumferences thereof with closure-accommodating baskets, wherein the conveying elements are drivable in opposite directions in a synchronous manner, wherein the conveying elements, together with external guiding means, define arcuate conveying section portions, and wherein the sterilizing region is provided at one of said arcuate conveying section portions.

14. The apparatus of claim 1, wherein the sterilizing region includes a first treatment station configured for applying a hot sterilizing medium containing hydrogen peroxide onto the closures, and a second treatment station following the first treatment station in the conveying direction, said second treatment station being configured for activating the hydrogen peroxide by heating.

15. The apparatus of claim 14, further comprising a third treatment station for impinging sterilizing medium upon the closures, and a fourth treatment station for preheating the closures, said fourth treatment station being disposed in the conveying direction upstream of the third treatment station.

16. The apparatus of claim 1, further comprising a heater associated with at least one treatment station in said sterilizing region.

17. The apparatus of claim 1, further comprising a mixing head associated with said sterilizing region for discharging sterilizing medium, said mixing head being configured to introduce hydrogen peroxide in finely distributed form into a vaporous and/or gaseous medium to generate the sterilizing medium.

18. The apparatus of claim 1, further comprising a sensor and a switch that is configured to switch said sterilizing region on and off in response to detection by said sensor of at least one of a number of closures treated per unit time, and conveying speed of the circulating conveying element, wherein the sterilizing region includes treatment stations disposed consecutively along the conveying direction and wherein the switching is carried out in such a manner that the number of treatment stations connecting to one another in the conveying direction activated for in each case one treatment step increases as the number of closures treated per unit time increases and/or as the conveying speed of the circulating conveying element increases, and decreases as the number of closures treated per unit time decreases or the conveying speed of the circulating conveying element decreases.

19. The apparatus of claim 1, wherein the circulating conveying element comprises a drum that is driven to rotate about a horizontal axis, wherein the sterilizing region is within the drum, and wherein webs or projections form the closure-accommodating basket on an inside surface of the drum.

20. The apparatus of claim 19, further comprising guiding means provided in an interior of the drum, said guiding means not being entrained with the drum and securing the closures against falling out of the closure-accommodating basket.

21. The apparatus of claim 19, wherein the sterilizing region comprises a treatment station at an angular region of the rotational movement of the drum.

* * * * *